(12) United States Patent
Campos

(10) Patent No.: US 8,221,311 B2
(45) Date of Patent: Jul. 17, 2012

(54) FACE TIP ASSEMBLY FOR AN ENDOSCOPE

(76) Inventor: Jorge A. Campos, Mexico City (MX)

( * ) Notice: Subject to any disclaimer, the term of this patent is extended or adjusted under 35 U.S.C. 154(b) by 1068 days.

(21) Appl. No.: 12/041,308

(22) Filed: Mar. 3, 2008

(65) Prior Publication Data

US 2008/0214895 A1 Sep. 4, 2008

Related U.S. Application Data

(60) Provisional application No. 60/904,253, filed on Mar. 1, 2007.

(51) Int. Cl.
*A61B 1/04* (2006.01)
*A61B 1/00* (2006.01)
*A61B 1/06* (2006.01)

(52) U.S. Cl. ........................... 600/129; 600/175
(58) Field of Classification Search .................. 600/104, 600/107, 127–130, 170, 171, 175, 160, 164
See application file for complete search history.

(56) References Cited

U.S. PATENT DOCUMENTS

| | | | | |
|---|---|---|---|---|
| 5,386,817 | A * | 2/1995 | Jones | 600/104 |
| 5,533,496 | A * | 7/1996 | De Faria-Correa et al. | 128/898 |
| 5,569,182 | A * | 10/1996 | Twardowski et al. | 604/43 |
| 2003/0028147 | A1 * | 2/2003 | Aves et al. | 604/164.06 |
| 2003/0040657 | A1 * | 2/2003 | Yamaya et al. | 600/107 |
| 2004/0153057 | A1 * | 8/2004 | Davison | 606/41 |
| 2004/0242963 | A1 * | 12/2004 | Matsumoto et al. | 600/127 |
| 2005/0043584 | A1 * | 2/2005 | Nozue | 600/127 |
| 2007/0038031 | A1 | 2/2007 | Miyagi et al. | |

FOREIGN PATENT DOCUMENTS

| | | |
|---|---|---|
| EP | 1741380 | 1/2007 |
| EP | 1743567 | 1/2007 |
| WO | WO 2005/048827 | 2/2005 |

OTHER PUBLICATIONS

International Search Report from PCT/US2008/055653.

* cited by examiner

*Primary Examiner* — Anhtuan Nguyen
*Assistant Examiner* — Alireza Nia
(74) *Attorney, Agent, or Firm* — Greenberg Traurig, LLP

(57) ABSTRACT

A face tip assembly for an endoscope for viewing a visually obscured portion of a body cavity and for surgically treating a portion of a body cavity with an operating tool may include at least one operating tool port located in an outer wall surface of the face tip assembly, and the outer wall surface may generally lie in a plane which is disposed at an acute angle with respect to the longitudinal axis of the face tip housing. This outer wall surface may have a generally U-shaped configuration. At least one optical image channel port may be located in another outer wall surface of the face tip housing, and this outer wall surface faces toward the distal end of the face tip housing. The outer wall surface in which the tool port is located extends from the outer wall surface in which the at least one optical image channel port is located, toward the distal end of the face tip housing.

10 Claims, 4 Drawing Sheets

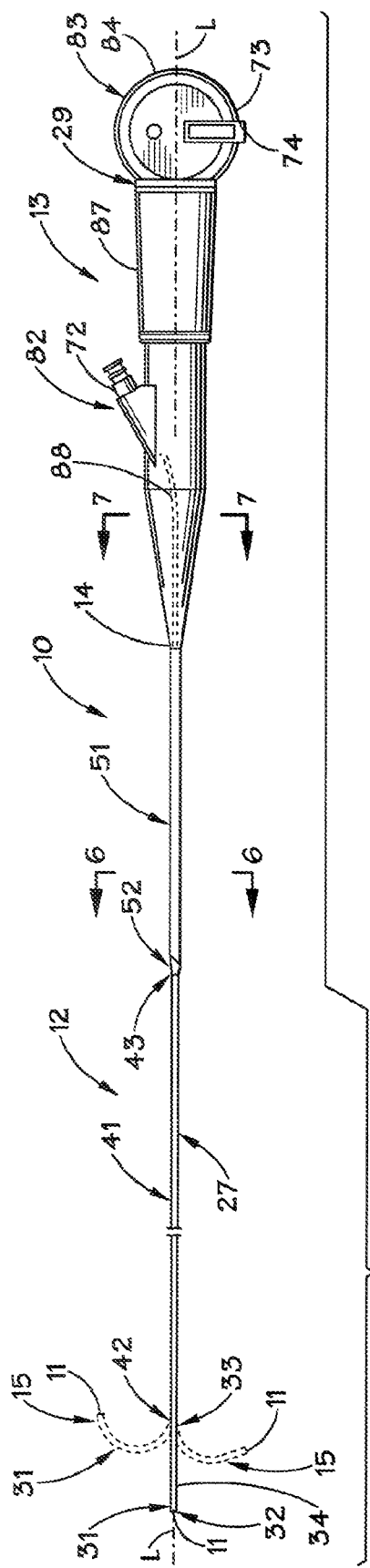
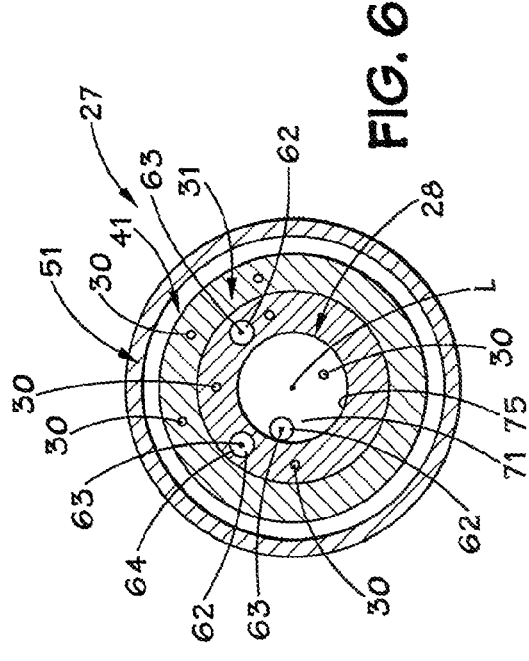
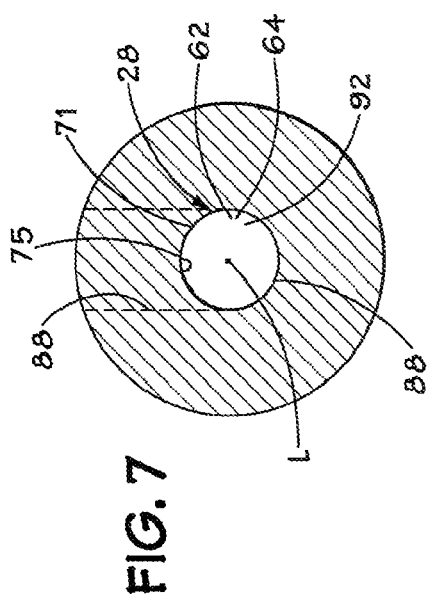
FIG. 1
FIG. 6
FIG. 7

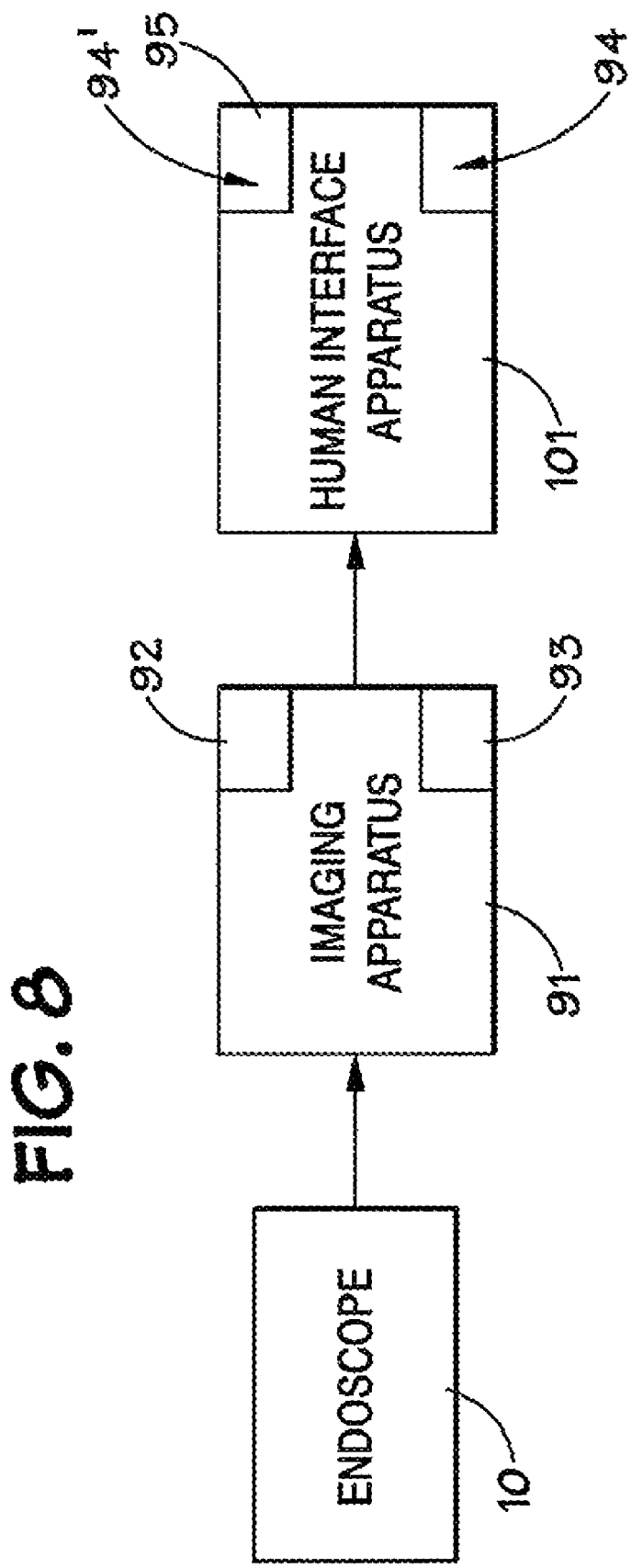

FACE TIP ASSEMBLY FOR AN ENDOSCOPE

RELATED APPLICATION

This application claims the benefit and priority benefit of U.S. Provisional Patent Application Ser. No. 60/904,253, filed Mar. 1, 2007, and entitled Face Tip For An Endoscope.

BACKGROUND OF THE INVENTION

1. Field of the Invention

The invention relates to exploratory instruments and, more particularly, to a face tip assembly, or, or face tip, for endoscopic type instruments.

2. Description of the Related Art

Endoscopic type instruments have been developed to allow physicians and surgeons to view within a visually obscured portion of a body cavity. Physicians and surgeons in particular use endoscopic type instruments in a body to perform certain surgical procedures with limited trauma, disfiguration, expense, and hazards usually associated with conventional types of surgery performed through relatively large incisions.

The design and elements of a traditional face tip, or face tip assembly, of an endoscopic type instrument, either rigid, semi-rigid or flexible, has changed very little since the first one was introduced. Basically they all include one or more of the following input/output ports: a working channel port to introduce operating accessories, or operating tools, to perform a procedure; an optical image collector port, for example, a telescope port for viewing; a luminous conductor port, for example, an illumination fiberoptics port; and sometimes an irritation and suction channel port. It is believed that with conventional endoscopes, the accessories, or tools, are introduced before they can actually be observed within the urinary system. The conventional operating accessories exit port is located behind the optics created a "blind spot"; thus they enter the urinary system before the surgeon has visual control. In the medical setting, the exit of the accessories, or tools, on the instrument's side is typically very close to the urinary tract wall. The surgeon's lack of view of the natural curves of the ureter, caused by the blind spot, may possibly produce an inadvertent tear or perforation of the ureteral wall. Also, by exiting the operating tools on the side of the instrument, it obligates the surgeon to rotate the instrument in order to appropriately target the lesion, or the foreign body, to achieve the purpose of the exploration or the intervention. This maneuver or "frequent rotation" may possibly increase the risk of perforation and/or the inherent trauma by the instrument's insertion or pressure creating inflammation of the structures under exploration.

The light source for illuminating the site of interest is usually positioned outside the cavity. The light is communicated through the instrument by an illumination, or light conductor, usually formed of a fiber optic bundle. Conventional lenses for image collection and transmission, or coherent optical fiber bundles wherein the opposite ends of the fibers are identically ordered may be utilized.

Endoscopic type instruments may be constructed to have fluid channels which may serve a variety of different purposes. For example, in certain procedures on the lungs, the fluid channel provides an air passage to allow the lung to breathe. In other procedures, the fluid channel may be used to insufflate, or inflate, a cavity in the body for better access to obtain a better view. In other procedures, a supply of cleansing fluid, such as water, may be used to clear away undesirable contaminant fluid, such as blood, from a location to facilitate inspection or to clean the image collector. A suction line is often used for removing fluids from the site. A working tool channel provides for the insertion of various working implements, or accessories, through the instrument such as forceps, scissors, punches, electrodes, lasers, and the like.

An endoscopic type instrument may include a typically tubular shaped shaft connected to a handle and viewing assembly which typically provide a mechanical coupling to which a viewing apparatus is connected. The typical endoscopic type instrument may include fluid channels extending through the shaft which communicate with external fluid connections on the handle and the assembly. A working tool port on the handle and viewing assembly typically communicates with a working tool channel in the shaft and may include a clamp or other support device to hold the working tool in place. An illumination port typically communicates with a light source. The light is normally transmitted from the viewing end or proximal end of the instrument to a light directing lens, or lenses, at the distal end. An optical collector including an objective lens is positioned at the distal end and passes the image through the image conductor to the handle and viewing apparatus through which the operator views the section of the cavity of interest. The objective lens, if used, is typically fixed and may be oriented along the longitudinal axis of the shaft or be angled off-axis for a view to the side. Some endoscopic type instruments have a fixed combination of functions, while others may be adapted to allow a selection of functions from a variety of working tools and viewing methodologies.

The handle and viewing apparatus of endoscopic type instruments usually accommodate various adapters for connecting various types of video, or other imaging, devices. In some cases, all image multiplexer is utilized to separate the image for simultaneous display on an optical viewer used for direct viewing and a video imager to televise or record the procedure.

SUMMARY OF THE INVENTION

In accordance with the illustrative embodiments hereinafter described, a face tip assembly for an endoscope for viewing a visually obscured portion of a body cavity and for surgically treating a portion of the body cavity with an operating tool may comprise: a face tip housing assembly for an endoscope for viewing a visually obscured portion of a body cavity and for surgically treating a portion of the body cavity with an operating tool, including a face tip housing, at least one optical image channel port, at least one optical image collector, at least one luminous conductor, at least one operating tool port, and the at least one operating tool port may be located in an outer wall surface of the face tip assembly. The outer wall surface may generally lie in a plane which is disposed at an acute angle with respect to the longitudinal axis of the face tip housing, and that outer wall surface may have a generally U-shaped configuration.

BRIEF DESCRIPTION OF THE DRAWINGS

The present face tip assembly for an endoscope may be understood by reference to the following description taken in conjunction with the accompanying drawing, in which:

FIG. 1 is a side view of an endoscope, such as a ureterscope, with which the present face tip assembly may be used;

FIG. 6 is a partial cross-sectional view of the endoscope of FIG. 1, taken along line 6-6 in FIG. 1;

FIG. 7 is a partial cross-sectional view of the endoscope of FIG. 1, taken along line 7-7 in FIG. 1; and FIG. 8 is a schematic diagram of a system for viewing a visually obscured portion of a cavity.

Figure 2:
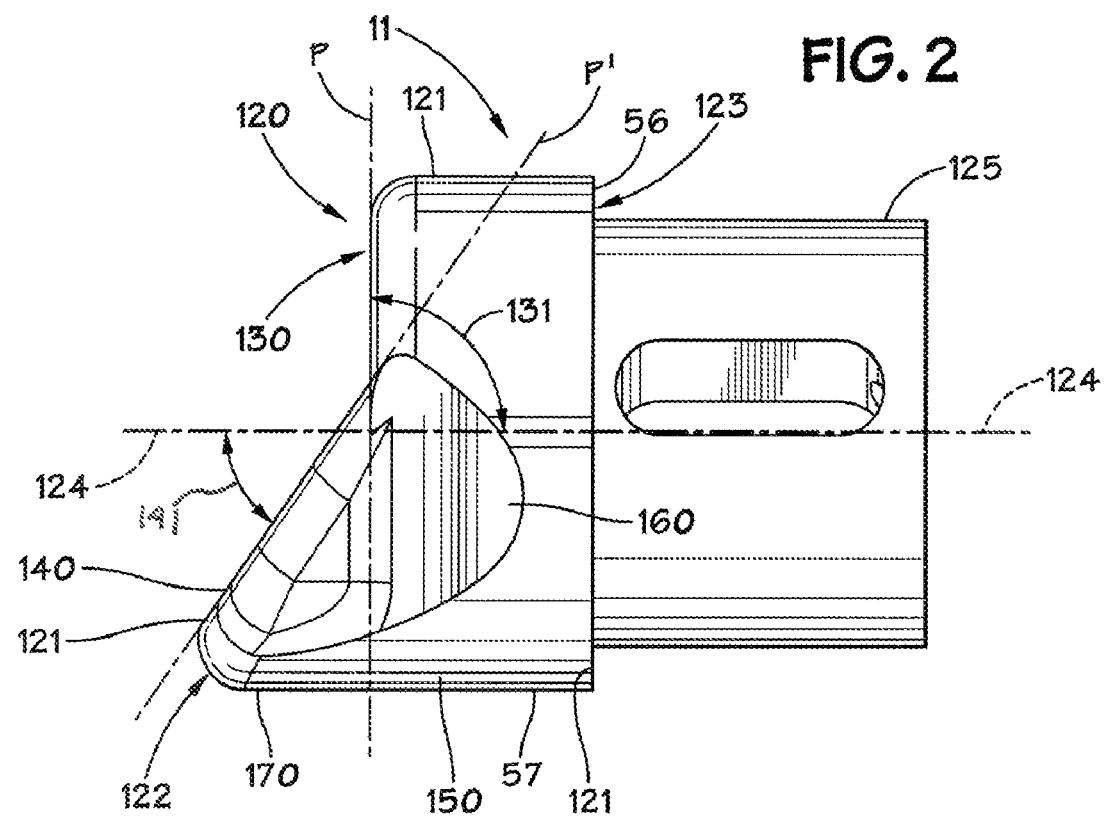
FIG. 2 is a side view of an illustrative embodiment of the present face tip assembly for use with the endoscope of FIG. 1.

While certain embodiments will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by the appended claims.

DETAILED DESCRIPTION OF SPECIFIC EMBODIMENTS

Illustrative, specific embodiments of the present face tip assembly for an endoscope are described below. The same reference numerals are used throughout this description and in the drawing for components having the same stricture, and primed reference numerals are used for components having a similar construction to those elements bearing the same unprimed reference numerals.

Referring now to the drawing, a ureteroscope 10 having a face tip assembly 11 is illustrated in FIGS. 1-5. This ureteroscope 10 is only one of many variations of endoscopes, or endoscopic type instruments, that can be used with the present face tip assembly 11. Ureteroscope 10 generally comprises: a face tip assembly 11 connected to a shaft, or shaft assembly 12, the shaft assembly 12 being connected to, or associated with, a handle and viewing assembly 13. In conjunction with the face tip assembly 11, the shaft assembly 12 provides for a reduced risk of laceration of a cavity by allowing the use, or viewing, of conventional, instrument accessories, or "operating tools" (not shown), by providing a tool exit, or port 21, in front of an optical image collector 61, FIGS. 3, 4, and 5. The shaft assembly 12 also: provides for simultaneous usage of both the viewing apparatus and an operating tool; facilitates exploration in such cavities as the upper urinary tract; and avoids the necessity for excessive rotation of instruments when targeting, or viewing, is required while working inside such sensitive cavities such as the ureter.

Referring now to FIGS. 2-5, an embodiment of face tip assembly 11 includes a plurality of input/output ports. The ports may include: an operating tool port, or tool exit, 21 where conventional operating accessories, or operating tools (not shown) may exit and are introduced; at least one optical image channel port 22, and at least one luminous channel port 23. The face tip assembly 11 may also include at least one fluid and/or suction channel port 24. The face tip assembly 11 also includes at least one optical image collector 61 interfaced with the at least one optical image channel port 22 of face tip assembly 11, for gathering an image from within the interior body cavity. The type of optical image collector 61 corresponds with the type of optical conductor 62 utilized in ureteroscope 10. For example, selection of an optical waveguide to implement the optical conductor 62 may result in the requirement for a lens, or prism, as an optical image collector 61. If the means for implementing the optical conductor 62 utilized is fiber optics, such as a fiber optics bundle or array, the face of the fiber-optics array may, in turn, be the only means required to collect the optical image for transmission through the optical conductor 62 through to the handle and viewing assembly 13, albeit, with reduced visual acuity. The face tip assembly design, of FIGS. 2-5, as well as other designs herein described, provides the ability to access the upper urinary system within the kidney and incorporates improved visibility so as to avoid the "blind spot" previously described.

Figure 3:
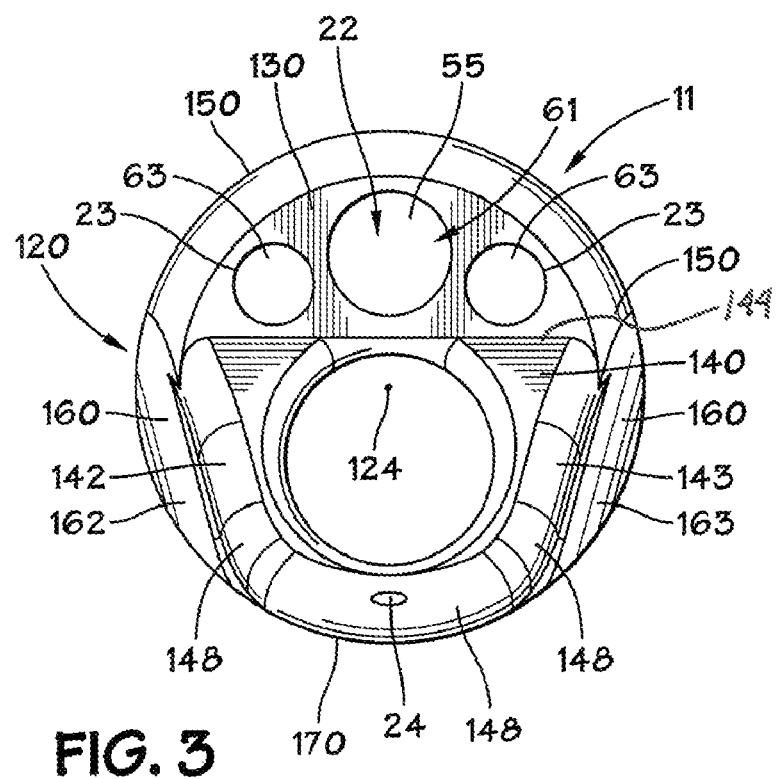
FIG. 3 is a front view of the face tip assembly of FIG. 2.
Figure 4:
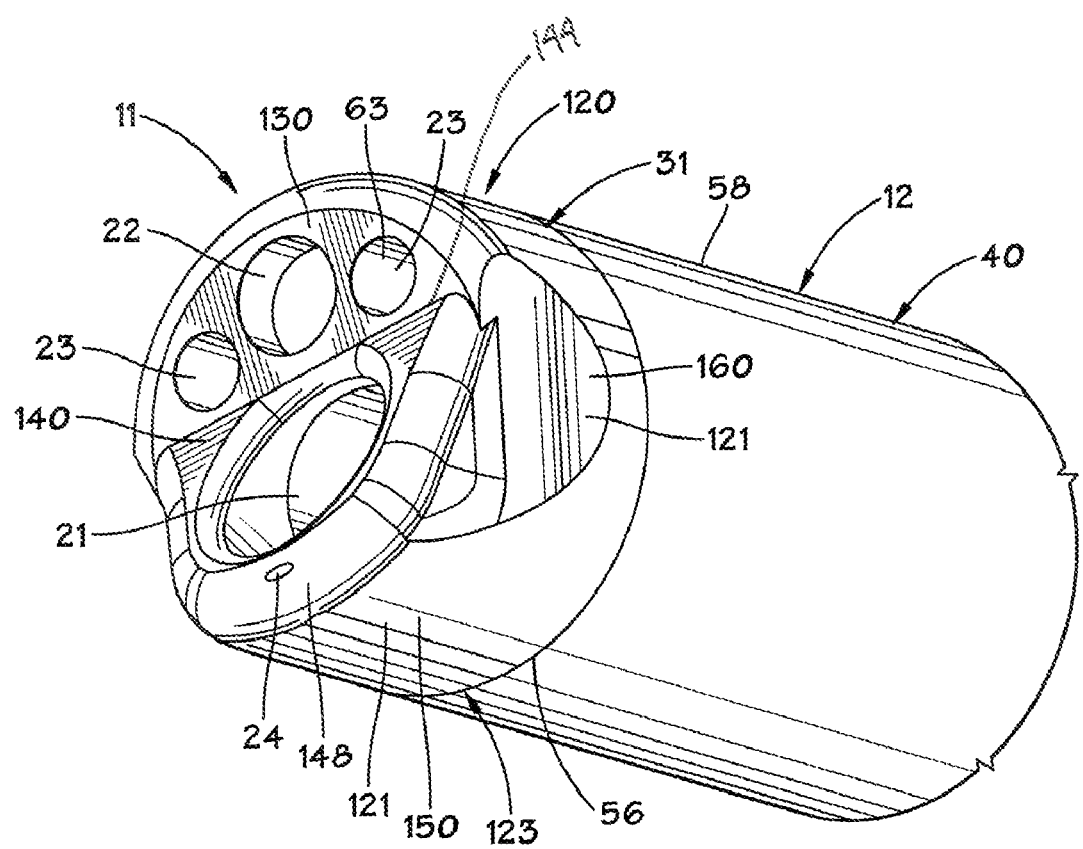
FIG. 4 is a perspective view of the face tip assembly of FIGS. 2 and 3 attached to an endoscope.
Figure 5:
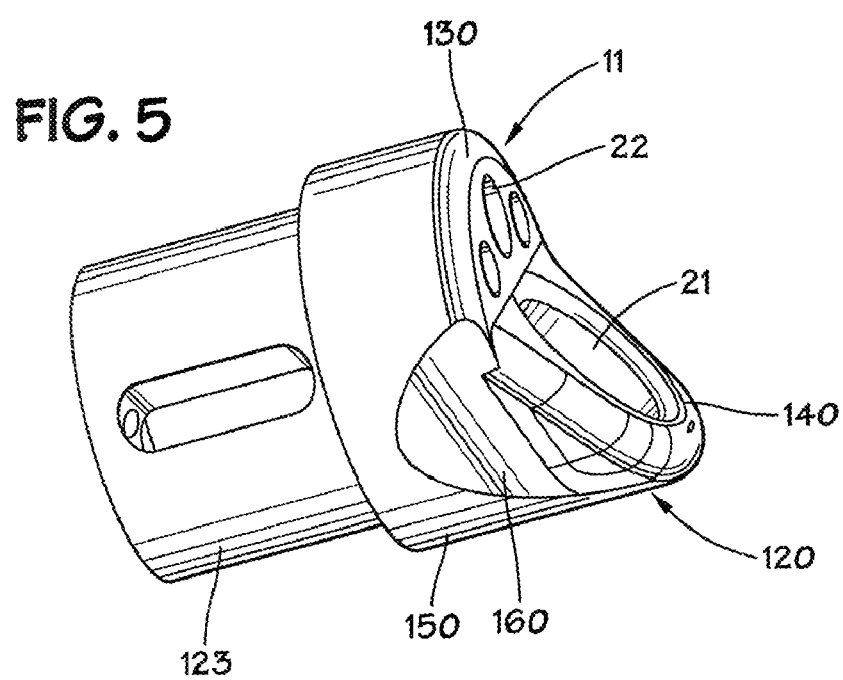
FIG. 5 is another perspective view of the face tip assembly of FIGS. 2 and 3.

An illustrative embodiment of the face tip assembly 11 is best shown in FIGS. 1-5. In this embodiment, the face tip assembly 11 is associated with, or connected to, the distal end 32 of a first flexible shaft segment 31 of shaft assembly 12. In this embodiment, where the distal end 32 has a substantially circular cross-sectional shape, the face tip assembly 11 has a substantially circular cross-sectional configuration as seen in FIG. 3. Face tip assembly 11 includes a face tip housing 120 having a plurality of outer wall surfaces 121, a distal end 122, a proximal end 123, and a longitudinal axis 124. As seen in FIGS. 2 and 5, face tip housing 120 may include a rearwardly extending insert body 125 which is received within, and secured to the distal end 32 of shaft assembly 12.

The face tip assembly 11 includes at least one optical image collector 61, which, in this embodiment may take the form of a lens 55. The lens 55 is preferably positioned in a plane P disposed substantially perpendicular to the longitudinal L axis of shaft assembly 12 and the longitudinal axis 124 of lace tip housing 120 (as shown in FIG. 2). Plane P may also be considered to be disposed substantially parallel to the interface 56 (FIG. 4) between face tip assembly 11 and the distal end 32 of flexible segment 31 of shaft assembly 12. As illustrated, the lens 55 is preferably spaced upwardly of the longitudinal axes L and 24. Face tip assembly 11 also includes an operating tool port 21. The face tip assembly's 11 outer perimeter 57 may be partially congruent with the outer perimeter 58 (FIG. 4) of the distal end 32 of the first flexible shaft segment 31. At least one luminous conductor 63 for light conduction and illumination, in the form of a fiber optics bundle, array, or a single fiber optic strand is located on face tip housing 120, as shown in FIG. 2. Preferably, two conductors 63 are utilized as shown in FIGS. 2 and 4.

As seen in FIGS. 2-5, face tip housing 120 is seen to have a first outer wall surface 130, and the first outer wall surface faces toward the distal end 122 of the face tip housing 120. Preferably, the at least one optical image channel port 22 is located in the first outer wall surface 130. The at least one operating tool port 21 is located in a second outer wall surface 140 of the face tip housing 120. As seen in FIG. 2, the second outer wall surface 140 generally lies in a plane P' which is disposed at an acute angle 141 with respect to the longitudinal axis 124 of the face tip housing 120. As seen in FIGS. 2-5, the second outer wall surface 140 extends from the first wall surface 130 toward the distal end 122 of the face tip housing 120. The at least one operating tool port 21 is formed in, or located in, the second outer wall surface 140. The luminous channel ports 23 with their associated luminous conductors 63 are formed in, or located within, first outer wall surface 130. As seen in FIG. 3, the second outer wall surface 140 has a generally U-shaped configuration having first and second opposed side edges 142, 143 as shown in FIGS. 2-5. The first and second opposed side edges 142, 143 of the second outer wall surface 140 have a generally rounded, curving configuration, which appear as rounded lips, or ridges, 148. This structure permits face tip assembly 11 to function in its desired manner, without having sharp edges which could possibly irritate or damage the body cavities filth which endoscope 10 is used, such as the urethra, bladder, ureters, and kidneys. The second outer wall surface 140 has an upper edge 144 which extends between the upper ends of opposed side edges 142, 143, and the upper edge 144 is located where the second outer wall surface 140 meets, or merges with, the first outer wall surface 130.

As seen in FIG. 2, the first outer wall surface 130 is preferably disposed substantially perpendicular to the longitudinal axis 124 of the face tip housing 120. It should be readily apparent that its annular disposition with respect to the longitudinal axis 124 could be varied, so long as the optical image collector 61 within optical image channel port 22 is able to adequately view an operating tool (not shown), such as a scissor, forceps, or other operating tool as are known in the art for use with endoscopes 12, as it exits from operating tool port 21 in a miner so that substantially no blind spot is present. In this regard, if desired, the angle 131 (FIG. 2) between the first outer wall surface 130 and longitudinal axis 124 may be greater than ninety degrees, provided the previously described blind spot is substantially avoided; or angle 131 may be an acute angle, whereby the first outer wall surface 130 lies in a plane which is substantially coplanar with the plane P' in which the second outer wall surface 140 lies.

Also with reference to FIG. 2, the acute angle 141 between the second outer wall surface 140 and the longitudinal axis 124 of face tip housing 120 preferably falls within a range of between twenty and seventy degrees. Preferably as shown in FIG. 2, acute angle 141 is approximately forty-five degrees. With reference to FIG. 3, the second outer wall surface 140 may have associated therewith, or adjacent thereto, at least one fluid and/or suction port 24. Although only one suction port 24 has been illustrated, if desired, additional fluid and/or suction ports 24 could of course be provided.

Still with reference to FIGS. 2-5, the face tip housing 120 is seen to have a generally cylindrical cross-sectional configuration, as clearly shown in FIG. 3, and this generally cylindrical cross-sectional configuration may be encompassed, or enclosed, by a third outer wall surface 150. The third outer wall surface 150 as seen in FIG. 2, may be disposed between the first outer wall surface 130 and the proximal end 123 of the face tip housing 120. Face tip housing 120 may also include fourth outer wall surfaces 160 which are associated with the first and second side edges 142, 143 of the second outer wail surface 140. For example, first and second, fourth outer wall surfaces 162, 163 may be provided. The first, fourth outer wall surface 162 is disposed adjacent the first opposed side edge 142, or lip 148, of the second outer wall surface 140 and adjacent the third outer wall surface 150. A second, fourth outer wall surface 163 is disposed adjacent the second opposed side edge 143, or lip 148, of the second outer wall surface 140, and fourth outer wall surface 163 is also disposed adjacent the third outer wall surface 150.

As seen in FIGS. 2-5, each fourth outer wall surface 160 generally lies in a plane which slopes outwardly away from the second outer wall surface 140 toward the third outer wall surface 150 in a direction toward the proximal end 123 of face tip housing 120. The fourth outer wall surfaces 160 may be considered to be formed by removing a portion of the third outer wall surface 150. When viewed from the side as seen in FIG. 2 or 4, the fourth outer wall surfaces have a shape which resembles a parabola. A fifth outer wall surface 170 is seen to generally underlie the second outer wall surface 140, and the fifth outer wall surface 170 is seen to generally lie in a plane parallel with the longitudinal axis 124 of the face tip housing 120. By forming face tip housing 120 in the manner previously described to include the second, third, fourth, and fifth outer wall surfaces, 140, 150, 160, and 170, the face tip housing 120 has a shape that is complementary to the ureteral orifice in the bladder, through which face tip assembly 11, along with section 31 of endoscope 10 must pass, in order to enter the ureter and from the ureter into the patient's kidney. The ureteral orifice is the opening in the bladder where the ureter empties urine. The ureteral orifice is often tight and may intermittently contract, thus potentially impeding advancement of the endoscope, or ureteroscope 10 into the ureter. The face tip housing 120 having a shape which is complementary to the uretral orifice assists in the passage of the endoscope 10 into the ureter.

Additionally, although the operating tool port 21, lenses 55, and the distal end 32 of first flexible segment 31 are depicted as having generally, circular cross-sectional configurations, it is important to note that in variations of this embodiments other geometric shapes as known by those of ordinary skill in the art, are within the spirit of the disclosure, such as elliptical, oval, or other shapes. Also, the distal end 32 of first flexible segment 31 may have a smaller circumference, or diameter, than the main shaft body 34 of first flexible shaft segment 31, whereby the outer perimeter 57 of face tip assembly 11 may be at least partially received around, and connected to, the smaller outer circumference of distal end 32. Still referring to FIGS. 2-5 face tip assembly 11, may include variations in the shape of outer perimeter 57, variations in the positioning, or location, of lens 55, operating tool port 21, and optical conductors 62. Additionally, in other embodiments of the face tip assembly 11 structure depicted in FIGS. 2-5, the optical image collector 61 may be in another form such as prisms or a substantially flush bundle of fiber optics or other methodologies as known by those of ordinary skill in the art. The optical conductor 62 and luminous conductors 63 may also be in any acceptable form as known by those of ordinary skill in the art that can perform substantially the same function as fiber optics.

In the illustrative embodiment of face tip assembly 11 depicted in FIGS. 2-5, monoptic, monoscopic, or two-dimensional viewing is provided as there is only a single optical image collector 61 utilized. If three-dimensional, or 3-D viewing is desired, an additional optical image collector 61 could be provided to provide the desired 3-D viewing. For example, the two luminous channel ports 23 could each be used to house an optical image collector 61, and optical image channel port 22 could be utilized to house a luminous conductor 63, or additional luminous conductor 63 could of course be provided.

Referring to FIGS. 1 and 6, the shaft assembly 12 of ureteroscope, or endoscope, 10 may include a shaft 27 having at least one longitudinally extending passageway 28 and handle and viewing assembly interface 29. Preferably, there is a passageway 28 which corresponds to, and is in communication with, each operating, tool port 21, optical image channel port 22, and luminous channel port 23. The shaft 27 is preferably constructed of a suitable nontoxic material, such as a plastic or polymer material and includes a first flexible shaft segment 31 having distal end 32 adapted for insertion into the cavity and interfaced with the face tip assembly 11 at interface 56; a second flexible shaft segment 41 having a distal end 42 connected to a proximal end 33 of the first flexible shaft segment 31; and a third shaft segment 51 having distal end 52 connected to a proximal end 43 of the second flexible shaft segment 41.

Preferably, the shaft 27 is constructed so that it has a substantially smooth, continuous outer surface, and its preferred cross-sectional configuration is circular. Preferably the length of the third shaft segment 51 is approximately 50 cm long. The first flexible shaft section 31 is preferably approximately 4 cm long, and the second flexible shaft section 41 is preferably approximately 20 cm long. The first and second flexible shaft sections 31, 41 preferably have cross-sectional configurations that are substantially uniform along their lengths, but they may taper downwardly toward the face tip assembly 11. The third section 51 of shaft 27 is constructed so that it has sufficient strength and rigidity to permit use within the bladder and to support the entry of the first and second flexible sections 31, 41 into the ureter by way of the ureteral orifices in the bladder leading to the ureters and may be described as rigid or semi-rigid in construction. The first and second flexible shaft sections 31, 41 are constricted in order to follow the contours of the ureter. Also, as is known by those of ordinary skill in the art of endoscopes, the lengths of the first segment 31, second segment 41, and third segment 51 of the shaft 27 may vary according to the intended use of the endoscope 10.

The third shaft segment 51 is dimensioned to be received in a human body so that it extends through the urethra and substantially through the bladder, The distal end 52 of segment 51 is tapered to receive the proximal end 43 of the second flexible segment 41 and is formed to provide a smooth, gradual transition between the second flexible segment 41 and the third segment 51, to permit the non-traumatic passage of the shaft 27 through the urethra and into the bladder. Preferably, the third section 51, preferably, has sufficient strength and rigidity to enable both axial and rotational translation with the maneuvering of the handle and viewing assembly 13, without excessive twisting of the shaft 27. Additionally, the connection 14 between shaft segment 51 and the handle and viewing assembly 13 has sufficient strength and rigidity to avoid breaking a during use and handling of endoscope 10. Thus, the user is able to insert the shaft 27, leading with face tip assembly 11, into the urethra and maneuver the instrument through the bladder in order to position the first flexible section 31 and thus the face tip assembly 11 into a ureteral orifice leading to a ureter. The first flexible segment 31 having distal end 32 adapted for insertion into the cavity is dimensioned to be received in the ureter of a patient.

The second flexible shaft segment 41 having a distal end 42, like first flexible shaft 31 is correspondingly also dimensioned to be received in the ureter of a patient and is sufficiently flexible along its length to follow various canals of the human body, such as the ureter. In order to optimize the versatility of a flexible endoscope while retaining the controllability of a rigid endoscope, the second flexible segment 41 is "passively flexible". The term "passively flexible" is intended to mean that shaft segment 41 may be moved, flexed, or bent, to assume a curved configuration, in response to forces exerted upon the shaft 27 as it passes through a cavity or body passageway, but the movement, flexing, or bending is not substantially controllable by the operator of the instrument. While the third shaft segment 51 provides the user with sufficient feel and control of the instrument 10, the second flexible segment 41 has the ability to readily flex and follow the contours of a cavity or passageway, such as the ureter, without excessive deformation of its cavity or passageway, in order to minimize any traumatic effects.

In contrast, the first flexible shaft segment 31 is "actively flexible". The term "actively flexible" is intended to mean that shaft segment 31 may be moved, flexed, or bent to assume a curved configuration, such as shown in phantom lines 15 in FIG. 1, or an angular disposition with respect to longitudinal axis L, and such movement, flexing or bending is substantially controlled by the operator, who can cause and control the desired movement, flexing, and/or bending. The deflection of face tip assembly 11 upon operator, or user, command, or control, aids the user in the detection and penetration of the opening, or ureteral orifice in the bladder leading to the ureter.

Additionally, the relatively small diameters of face tip assembly 11 and first flexible shaft segment 31 allow the user to insert the shaft 27 into the ureteral orifice in the bladder leading to the narrow opening of the ureter to gain access to the ureter and kidney. The active flexibility of the first flexible shaft segment 31 also provides for non-traumatic use of the instrument 10 and precise positioning of the face tip assembly 11 adjacent to items of interest such as a lesion or kidney stone. Most significantly, the actively flexible first flexible segment 31 enables the user to view and non-traumatically deliver a working tool via the working channel 71 and operating tool port 21 to the item of interest. The flexibility of the first flexible segment 31 generally negates the need for rotating the instrument when targeting or advancing the instrument as required.

The first flexible shaft segment 31 may be made actively flexible using various methodologies. The first flexible segment 31 may be made actively flexible through use of operating, or guide, wires 30 guided through individual conduits which pass longitudinally through shaft segment 31 or a through passageway 28 within shaft 27 toward the distal end 32, which wire, or wires, may be manipulated, or pulled, so as to bend, move, or flex, the shaft segment 31 in a desired direction. The distal ends of the wires 30 may be suitably anchored adjacent the distal end 32 of shaft segment 31, whereby upon pulling on the wire, or wires 30, the desired controlled flexing, moving, or bending will occur. Alternatively, the first flexible shaft segment 31 may be comprised of a connected string of body members consisting of semicircular disc-like ring elements forming selectively controllable expandable bodies, whereby upon controlled expansion of selected ring elements, the shaft segment 31 moves or flexes in the desired direction, similar to the manner in which a snake moves. Other methodologies for providing the requisite flexibility could include the use of springs, separate wire guides, or the working tool itself, among others. If desired, the cross-sectional shape of first flexible shaft segment 31 could be varied in order to provide varying inherent flexibility characteristics. In other words, one or more portions, or sides, of the first flexible shaft segment 31 can be made to be more pliable, or flexible, than other portions, or sides, of the same first flexible shaft segment in order to make a shaft segment that more readily flexes in a first direction and is more rigid in a second direction.

Alternatively, the first flexible shaft segment 31 can be made from a composite material that has differing properties that will result in having a first flexible segment 31 predisposed to more readily bend, or flex, in a first direction, for example, upwardly and downwardly, rather than from side to side. Alternatively, the active desired flexibility of the first flexible shaft segment 31 could be obtained by use of a longitudinally disposed tension cable filth a distal spring deflection recovery member, whereby increased tension or compression on the tension cable initiated through a suitable control causes the flexible shaft segment 31 to deflect or flex in a desired direction.

With reference to FIGS. 1, 6, and 7 the handle and viewing assembly 13 has a plurality of passageways, or channels, 88 in communication with corresponding passageways, or channels, 28 of shaft 27 and longitudinally extend to the first flexible shaft segment 31 to the input/output ports of the face tip assembly 11. The passageways, or channels, between face tip assembly 11 and handle and viewing assembly 13 may be of equal diameter, or of differing diameter sizes, whereby they taper from one end to another to provide a smooth continuation of the passageways or channels.

With reference to FIGS. 1, 6, and 7, the handle and viewing assembly 13 includes: a distal section 81 which connects, or interfaces, with shaft 27, a working channel interface section 82 including a working channel interface assembly 72 which provides access for various operating tools through the instrument 10; a luminous conductor interface assembly 73 which provides for connecting, or interfacing, a light source such as a lamp box, for example with the luminous conductor 63; and a proximal section 83 including proximal section assembly 84, including optical channel interface assembly 74, and which provides either an interface, or an intermediate connection, to a conventional imaging apparatus (not shown). The handle and viewing assembly 13 may include, if desired, any one or more of the following connection components: a handhold or pistol-type grip; a telescopic viewing assembly; an eyepiece adjustment, an optical tap for transmission of the optical image to an imaging apparatus; an electronic image enhancer/transmitter; and/or valve(s) for irrigation/suction.

The instrument 10 includes a working channel 71 for providing a pathway into the internal cavity for a conventional working instrument. Referring now to FIGS. 1, 2, 6 and 7, the working channel 71 is formed via passageways 28, 88 and provides working tool access to the interior cavity, the channel 71 extending from the working channel interface assembly 72 through to the operating tool port 21. The working channel 71 has a substantially smooth interior surface to provide smooth movement of a working tool through instrument 10. The working channel 71 may have a substantially circular cross-sectional configuration, and may be coaxially surrounded by shaft segments 31, 41, and 51 of shaft 27. The interior wall surface 75 of working channel 71 may be coated with, or formed of, a material having a reduced coefficient of friction to facilitate easy passage and use of working accessories, or tools, in the working channel 71.

The instrument 10 includes at least one luminous conductor 63 for providing illumination within the interior cavity. The luminous conductor 63 extends from the luminous conductor interface assembly 73 of handle and viewing assembly 13, through shaft 27, to distal end 32 of first flexible shaft segment 31 to face assembly 11. The luminous conductor 63 is in the form of a fiber optic light carrying bundle. The luminous conductor interface assembly 73 provides a connector, as understood by those skilled in the art, between the luminous conductor 63 (light guide) and a conventional light source (not shown). Light travels through the luminous conductor interface assembly 73 and through the handle and viewing assembly housing 87 and shaft 27 to the interior cavity in a manner depending upon the configuration of the face tip assembly 11. For example, the luminous conductor 63 may be a single fiber optic bundle, or a plurality of independent fiber-optic bundles, or a single fiber-optic bundle divided prior to, or upon reaching, luminous channel port 23. Also, in an embodiment, the luminous conductor interface assembly 73 may include an adjustable light valve (not shown) for selectively adjusting the intensity of the light. In another embodiment, the handle and viewing assembly 13 may include a plurality of the luminous conductor interface assemblies 73.

Referring again to FIGS. 1 and 6, an embodiment of the present face tip assembly also comprises at least one optical conductor 62 optically interfaced with the optical collector 61 for transmitting the gathered interior cavity image to the handle and viewing assembly 13. In this embodiment, the optical conductor 62 is in the form of a fiber-optic bundle 64. In this embodiment, the instrument 10 includes an optical conductor channel 92 which encloses and receives the optical conductor 62, 64. The optical conductor 62, 64 may be located within the instrument 10, such as by disposing it in the working channel 71, or it may be formed as a separate channel. A luminous conductor channel 93 may be provided to carry light to the face tip assembly 11 and correspondingly the internal cavity and thus, the area of interest. A fused fiber optic image bundle 62 would extend through shaft 27 to the face tip assembly 11 and correspondingly to the optical image collector 61. In an embodiment, the optical conductor 62 is supported within handle and viewing assembly housing 87 by means known by those skilled in the art. For example, the optical conductor 62 would be supported within the handle and viewing assembly housing 87. The handle and viewing assembly 13 of endoscope 10 may be equipped to interface with an imaging apparatus 91 (FIG. 8) having an imaging, processor 93 in order to capture the image gathered by optical image collector 61 in order to process the image for transmission to a human interface apparatus 101, such as a monitor and/or to video capable glasses. In an alternative embodiment, the handle and viewing assembly 13 is used as a form of telescope as known by those skilled in the art, whereby an ocular lens and lens support would cooperate with a spring means to permit relative movement between the optical conductor 62 and the housing 87 to provide direct, adjustable, visual imaging. In an embodiment, an optical wedge (not shown) is included, the optical wedge can be located near the distal end 32 of the first flexible segment 31 to provide a direction of view compensation of about 5-10 degrees when viewed under water, as would be the case if implemented as a ureteroscope.

Referring now to FIGS. 1, 2, and 8, a system to view a visually obscured portion of a body cavity will be described. The system may include an endoscope 10 as previously described, or other endoscopes. The system may further include an imaging apparatus 91 coupled with the at least one optical conductor 62 via the handle and viewing assembly 13, for capturing the image to send it to a human interface apparatus 101. In an embodiment, instead of the user strictly viewing the image gathered by the optical image collector 61 through a telescope or eye piece portion of a viewing assembly as is the case with much of the state-of-the-art, the handle and viewing assembly 13 of the present invention may include a proximal section assembly 84 which provides an interface for the imaging apparatus 91 as known by those skilled in the art. In an embodiment, the imaging apparatus 91 is an image transceiver 92 including an image processor 93 capable of providing video output to a human interface apparatus 101. In another embodiment, the imaging apparatus 91 is a pair of cameras optically coupled with a plurality of optical conductors 62. The preferred function of the imaging apparatus 91 is to render a three-dimensional image of the area of interest as selected by the user. Typically this is accomplished using individual "optical feeds." Additionally, in the preferred embodiment utilizing a pair of optical conductors 62 and optical image collectors 61, the imaging apparatus 91 captures each half of the image to render a complete and broader view of the area of interest.

The system may include a human-interface apparatus 101, as shown in FIG. 8. The human interface apparatus 101 is electrically or optically coupled with the imaging apparatus 91. In various embodiments, the human interface apparatus 101 may include such display/interface devices including a first image display device 94 such as a CRT, HDTV, for example, and in the preferred embodiment a second image display device 94 including a video stereoscopic viewer unit 95 as known and understood by those skilled in the art. Although visual clarity is an important feature of the human interface apparatus 101, the invention is not limited to, or to the quality of, the examples provided above.

In the drawing and specification, there has been disclosed a typical preferred embodiment of the invention, and although specific terms are employed, the terms are used in a descriptive sense only and not for purposes of limitations. The illustrative embodiment has been described in considerable detail with specific reference to these illustrated embodiments. It will be apparent, however, that various modifications and changes can be made within the spirit and scope of the invention as described in the foregoing specification. It is understood that other materials and dimensions may be used for the endoscopic type instrument and present face tip assembly keeping in mind the dimensions of the affected body parts. Further, the number and dimensions of the channels or passageways employed are variable depending on the accessories (i.e. dye laser, fiber optics, etc.) used in conjunction with the instrument and face tip assembly. The face tip assembly may be used with any type of endoscopic instrument or shaft assembly. Also, other shaped handles and handles of other designs may be used. Accordingly, the invention is to be limited only by the scope of the appended claims.

What is claimed is:

1. A face tip assembly for an endoscope for viewing a visually obscured portion of a body cavity and for surgically treating a portion of the body cavity with an operating tool, comprising:
   a face tip housing having a plurality of outer wall surfaces, a distal end, a proximal end, and a longitudinal axis;
   at least one optical image channel port;
   at least one optical image collector associated with the at least one optical image channel port and adapted to gather an image from within the body cavity;
   at least one luminous conductor adapted to provide illumination to at least a portion of the body cavity;
   at least one operating tool port adapted to permit the operating tool to pass outwardly from the face tip housing into the body cavity;
   the at least one optical image channel port is located in a first outer wall surface of the face tip housing, the first outer wall surface facing toward the distal end of the face tip housing;
   the at least one operating tool port is located in a second outer wall surface of the face tip assembly, the second outer wall surface generally lies in a plane which is disposed at an acute angle with respect to the longitudinal axis of the face tip housing, and the second outer wall surface extends from the first wall surface toward the distal end of the face tip housing;
   the second outer wall surface has a generally U-shaped configuration having first and second opposed side edges;
   a third outer wall surface disposed between the first outer wall surface and the proximal end of the face tip housing;
   a first, fourth outer wall surface disposed adjacent the first opposed side edge of the second outer wall surface and the third outer wall surface;
   a second, fourth outer wall surface disposed adjacent the second opposed side edge of the second outer wall surface and the third outer wall surface; and
   each fourth outer wall surface generally lies in a plane which slopes outwardly, with respect to the longitudinal axis of the face tip housing, and away from the second outer wall surface toward the third outer wall surface and toward the proximal end of the face tip housing.

2. The face tip assembly of claim 1, wherein a portion of the face tip housing has a generally cylindrical cross-sectional configuration encompassed by the third outer wall surface.

3. The face tip assembly of claim 1, wherein the first outer wall surface generally is disposed substantially perpendicular to the longitudinal axis of the face tip housing.

4. The face tip assembly of claim 1, wherein the at least one luminous conductor is located on the first outer wall surface.

5. The face tip assembly of claim 1 including at least one suction port located adjacent the second outer wall surface.

6. The face tip assembly of claim 1, wherein the second outer wall surface generally lies in a plane which is disposed at an acute angle to the longitudinal axis of the face tip housing, and the acute angle is between twenty and seventy degrees.

7. The face tip assembly of claim 6, wherein the acute angle is approximately forty-five degrees.

8. The face tip assembly of claim 1, wherein the face tip housing has a fifth outer wall surface generally underlying the second outer wall surface, the fifth outer wall surface generally lies in a plane parallel with the longitudinal axis of the face tip housing.

9. The face tip assembly of claim 8, wherein the face tip housing, including the second, third, fourth, and fifth outer wall surfaces define a shape that is complementary to a ureteral orifice, whereby the face tip housing may easily be inserted into a ureteral orifice and into a ureter.

10. The face tip assembly of claim 1, wherein each fourth outer wall surface has a shape which resembles a parabola.

* * * * *

UNITED STATES PATENT AND TRADEMARK OFFICE
CERTIFICATE OF CORRECTION

PATENT NO. : 8,221,311 B2
APPLICATION NO. : 12/041308
DATED : July 17, 2012
INVENTOR(S) : Jorge A. Campos It is certified that error appears in the above-identified patent and that said Letters Patent is hereby corrected as shown below:

In Col. 1, line 32, delete "irritation" and insert --irrigation--.

In Col. 1, line 36, delete "created" and insert --creating--.

Signed and Sealed this
First Day of January, 2013

David J. Kappos
*Director of the United States Patent and Trademark Office*